United States Patent [19]

Nishiyama et al.

[11] 4,134,751
[45] Jan. 16, 1979

[54] HERBICIDAL COMPOUND, HERBICIDAL COMPOSITION CONTAINING THE SAME AND METHOD OF USE THEREOF

[75] Inventors: Ryuzo Nishiyama, Takatsuki; Kanichi Fujikawa, Kyoto; Rikuo Nasu, Kusatsu; Itaru Shigehara, Kusatsu; Nobuyuki Sakashita, Kusatsu, all of Japan

[73] Assignee: Ishihara Sangyo Kaisha Ltd., Osaka, Japan

[21] Appl. No.: 787,640

[22] Filed: Apr. 14, 1977

[30] Foreign Application Priority Data

Apr. 14, 1976 [JP] Japan .................................. 51/42952

[51] Int. Cl.$^2$ ...................... A01N 9/22; C07D 213/64
[52] U.S. Cl. ........................................ 71/94; 546/261; 546/302; 546/300
[58] Field of Search .... 260/245 R, 295 AM, 294.8 R; 71/94

[56] References Cited

U.S. PATENT DOCUMENTS 3,954,442  5/1976  Becker et al. ........................... 71/94
4,046,553  9/1977  Takahashi et al. ................ 260/294.8

*Primary Examiner*—Richard Raymond
*Attorney, Agent, or Firm*—Sughrue, Rothwell, Mion, Zinn and Macpeak

[57] ABSTRACT

Phenoxy valeric acids and derivatives thereof represented by the general formula (I):

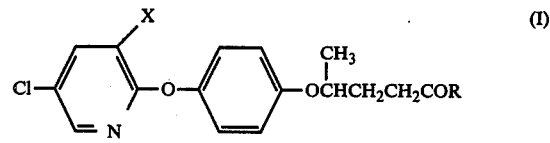

wherein X is a hydrogen atom or a chlorine atom; and R is a hydroxy group, an —O-cation group, a ($C_1$ - $C_4$)alkoxy group, a ($C_1$ - $C_4$)alkylthio group, a benzyloxy group, or an amino group which may be substituted with a ($C_1$ - $C_4$)alkyl group(s), a phenyl group or a pyridine-2-yl group, useful as a herbicide; a herbicidal composition containing the compound; and methods of controlling weeds using such materials.

15 Claims, No Drawings

HERBICIDAL COMPOUND, HERBICIDAL COMPOSITION CONTAINING THE SAME AND METHOD OF USE THEREOF

BACKGROUND OF THE INVENTION

1. Field of the Invention

This invention relates to a compound useful as a herbicide for agriculture and horticulture, to a herbicidal composition containing the same, and to methods of controlling weeds.

2. Description of the Prior Art

Hitherto, various herbicides have been developed and practically used for contributing to a saving of man power and increasing the yields of agricultural products, but there is much room for improvement in such herbicides and the development of new and useful herbicides has been strongly desired. It is, of course, desirable to develop, for example, herbicides which are safe from the standpoint of environmental pollution and which have the least adverse effect on useful plants, still retaining strong herbicidal activities, but in view of the fact that the resistance of weeds to existing herbicides has increased recently, the demand for herbicides which have higher activity and are different types from existing herbicides has increased.

SUMMARY OF THE INVENTION

One object of the present invention is to provide phenoxy valeric acids and derivatives thereof which have advantageous herbicidal properties.

A further object of the present invention is to provide an effective herbicidal composition.

Still a further object of the invention is to provide a method for controlling weeds.

Accordingly, this invention, in one embodiment, provides phenoxy valeric acids and derivatives thereof represented by the general formula (I):

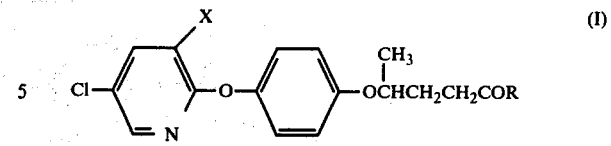

wherein X is a hydrogen atom or a chlorine atom; and R is a hydroxy group, an —O-cation group, a $(C_1-C_4)$alkoxy group, a $(C_1-C_4)$alkylthio group, a benzyloxy group, or an amino group which may be substituted with a $(C_1-C_4)$ alkyl group(s), a phenyl group or a pyridine-2-yl group.

In another embodiment, this invention provides a herbicidal composition comprising a herbicidally effective amount of at least one compound of the above general formula (I) and one or more agriculturally acceptable adjuvants.

In an even further embodiment of this invention, this invention provides a method of controlling weeds comprising applying a herbicidally effective amount of the above herbicidal composition to the weeds.

DETAILED DESCRIPTION OF THE INVENTION

In the definitions with respect to the formula (I) representing the compound of this invention, the cation can be a salt forming atom such as sodium, potassium, magnesium, calcium, etc., or a salt forming residue such as an ammonium group, an organic amine, etc.; and the alkyl moiety in the $(C_1-C_4)$alkoxy group, a $(C_1-C_4)$alkylthio group and a $(C_1-C_4)$alkyl group can be a methyl, ethyl, n-propyl, isopropyl, n-butyl, isobutyl, sec-butyl or tert-butyl group.

The compound of this invention of the formula (I) can be prepared by the following methods.

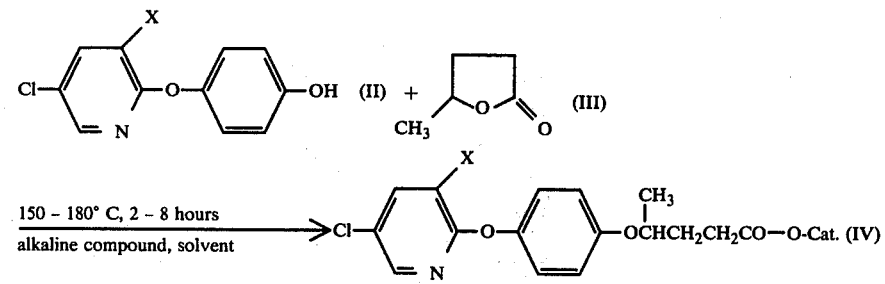

In the above reaction scheme, X is as defined above, and Cat. is a cation such as sodium or potassium.

Suitable examples of alkaline compounds used in the above reaction are sodium hydroxide, potassium hydroxide, etc., and suitable examples of solvents used in the above reaction are chlorobenzene, dichlorobenzene, toluene, xylene, butanol, amyl alcohol, etc.

Method (B)

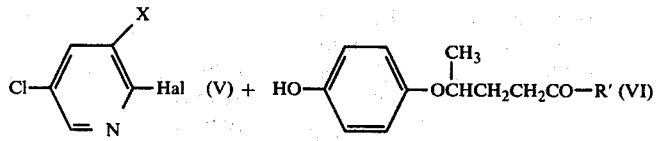

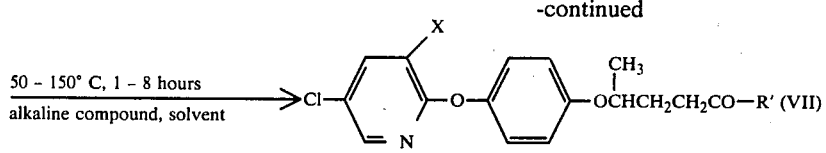

In the above reaction scheme, X is as defined above, Hal is a halogen atom, and R' is a (C$_1$-C$_4$)alkoxy group, a (C$_1$-C$_4$)alkylthio group, a benzyloxy group, or an amino group which may be substituted with a (C$_1$-C$_4$)alkyl group(s), a phenyl group or a pyridine-2-yl group.

Suitable examples of alkaline compounds used in the above reaction are sodium hydroxide, potassium hydroxide, sodium carbonate, potassium carbonate, etc., and suitable examples of solvents used in the above reaction are dimethyl sulfoxide, dimethylformamide, etc.

The resulting compound of the formula (IV) or the formula (VII) can be converted to the acids, salts, esters or amides of the formula (I) by the following known methods.

The resulting compound of the formula (IV) or (VII) is reacted with an acidic or basic material to form a phenoxyvaleric acid having the formula (VIII):

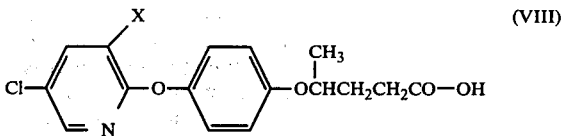

The phenoxyvaleric acid having the formula (VIII) is further reacted with an alcohol or an amine to form an ester or an amide.

The following Preparation Examples are given to illustrate the preparations of some typical compounds of this invention, but they are not to be construed as limiting the present invention. Unless otherwise indicated, all parts, percents, ratios and the like are by weight.

PREPARATION EXAMPLE 1

Preparation of Methyl-γ-[4-(5-chloropyridyl-2-oxy)phenoxy]-valerate

To a mixture of 14.8 g of 2,5-dichloropyridine, 27 g of methyl-γ-(4-hydroxyphenoxy)valerate and 16.5 g of potassium carbonate was added 40 ml of dimethyl sulfoxide. The reaction was performed at a temperature of 70° to 80° C. for about 3 hours with stirring. The reaction product was poured into an appropriate amount of water, extracted with chloroform, washed with water, and then dried over anhydrous sodium sulfate. The chloroform was evaporated off. Subsequent distillation under reduced pressure afforded 27.5 g of the final product having a boiling point of 180° to 200° C./1.5 mmHg.

PREPARATION EXAMPLE 2

Preparation of Methyl-γ-[4-(3,5-dichloropyridyl-2-oxy)phenoxy]-valerate 51.2 g of 4-(3,5-dichloropyridyl-2-oxy)phenol was dissolved in 120 ml of toluene, and an aqueous solution consisting of 9.6 g of sodium hydroxide and 10 g of water was then added to the resulting mixture to form the sodium salt of the above-described phenol. The thus obtained sodium salt was subjected to azeotropic dehydration with toluene under heating while stirring. At the time when the liquid temperature became 150° C., 22 g of γ-valerolacton was dropwise added to the solution, followed by allowing the resulting solution to react at around 170° C. for 8 hours. The reaction product was cooled and then thrown into an appropriate amount of a 10% sodium hydroxide aqueous solution. The extraction with diethyl ether was subsequently proceeded under acidic conditions with hydrochloric acid. The extraction layer was washed with water and dried over anhydrous sodium sulfate. The diethyl ether was then evaporated off to obtain γ-[4-(3,5-dichloropyridyl-2-oxy)phenoxy]valeric acid having a melting point of 97° to 99° C. Thereafter, 80 ml of methanol and 10 g of a 51% boron trifluoride/methanol complex salt were added thereto, and the resulting mixture was allowed to react under reflux for 3 hours. The product thus obtained was distilled under reduced pressure to obtain 58 g of the desired product having a boiling point of 215° to 220° C./2 mmHg.

Typical compounds prepared by the above methods are listed below. Reference by compound number designation set forth below will be made hereinafter in the specification.

---

Compound No. 1
Methyl-γ-[4-(5-chloropyridyl-2-oxy)phenoxy]valerate
b.p. 180 – 200° C/1.5 mmHg Compound No. 2
Sodium-γ-[4-(5-chloropyridyl-2-oxy)phenoxy]valerate Compound No. 3
Methyl-γ-[4-(3,5-dichloropyridyl-2-oxy)phenoxy]valerate
b.p. 215 – 220 ° C/2 mmHg Compound No. 4
Isopropyl-γ-[4-(3,5-dichloropyridyl-2-oxy)phenoxy]valerate
b.p. 232 – 235° C/2 mmHg Compound No. 5
γ-[4-(3,5-Dichloropyridyl-2-oxy)phenoxy]valeric Acid
m.p. 97 – 99° C Compound No. 6
Sodium-γ-[4-(3,5-dichloropyridyl-2-oxy)phenoxy]valerate Compound No. 7
Benzyl-γ-[4-(3,5-dichloropyridyl-2-oxy)phenoxy]valarate
b.p. 219 – 221° C/2 mmHg Compound No. 8
γ-[4-(3,5-Dichloropyridyl-2-oxy)phenoxy]valeric Acid Ethylthio Ester
b.p. 212 – 214° C/2 mmHg Compound No. 9
γ-[4-(3,5-Dichloropyridyl-2-oxy)phenoxy]valeramide Compound No. 10
N,N-Diethyl-γ-[4-(3,5-dichloropyridyl-2-oxy)phenoxy]valeramide
b.p. 176 – 180 ° C/4 mmHg Compound No. 11
γ-[4-(3,5-Dichloropyridyl-2-oxy)phenoxy]valeranilide
b.p. 202 – 207° C/3 mmHg Compound No. 12
N-2-Pyridyl-γ-[4-(3,5-dichloropyridyl-2-oxy)phenoxy]valeramide
b.p. 258 – 263° C/2 mmHg

---

Herbicidal compositions containing the compounds of the present invention having the formula (I) above as active ingredients exhibit excellent herbicidal activities as shown in the Test Examples hereinafter described. In particular, it is noted that the compounds exhibit a peculiar selective herbicidal activity on gramineous weeds without causing any phytotoxic activity on broad leaved crops. Thus, by taking advantage of such selective herbicidal activities of the compounds, the herbicidal compositions of this invention make it possible to control only noxious gramineous weeds which grow in crops cultivated on upland farms by applying the compositions in various application manners. Of course, the herbicidal compositions of the present invention can also be applied broadly to orchards, forests, various nonagricultural lands, paddy fields (low land fields) in addition to the upland farms by suitably selecting the application procedure, the amount of the composition to be used, etc. Also, such herbicidal compositions can be applied using various techniques such as soil treatment, foliar treatment and the like in a similar manner to conventional herbicidal compositions, as is well known in the art.

A suitable rate of application varies according to various factors such as the climatic conditions, the soil conditions, the form of the chemical, the time of application, the method of application, or the types of cultivated crops to which it is applied and the main weeds to be controlled. Usually the amount of the active ingredient is about 0.1 to about 1,000 g per are (100 $m^2$), preferably 1 to 500 g per are, and more preferably 5 to 100 g per are.

The compound of this invention can be dispersed in water to produce an aqueous dispersion.

The compound of this invention can also be formulated into various forms such as an emulsifiable concentrate, a wettable powder, a water-miscible solution, a dust or granules by optionally incorporating conventional agriculturally acceptable adjuvants, for example, a carrier such as diatomaceous earth, calcium hydroxide, calcium carbonate, talc, white carbon, kaolin, bentonite or Jeeklite (trade name for kaolinite, produced by Jeeklite Co.), a solvent such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester or a polyoxyethylene sorbitan fatty acid ester. A suitable ratio of the compound of this invention to the adjuvant(s) ranges from about 1 to 90:99 to 10 by weight, preferably 1 to 70:99 to 30 by weight.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such joint usage brings about improved effects.

Typical examples of herbicidal formulations containing a compound of this invention are shown below.

FORMULATION EXAMPLE 1

| | |
|---|---|
| (1) Methyl-γ-[4-(5-chloropyridyl-2-oxy)-phenoxy]valerate | 20 wt. parts |
| (2) Xylene | 60 wt. parts |
| (3) Sorpol 2806B (trade name for a mixture of polyoxyethylene phenyl phenol derivative, a polyoxyethylene alkylaryl ether, a polyoxyethylene sorbitan alkylate and an alkylaryl sulfonate produced by Toho Chemical Co.,Ltd.) | 20 wt. parts |

The components (1) to (3) were uniformly mixed to form an emulsifiable concentrate.

FORMULATION EXAMPLE 2

| | |
|---|---|
| (1) Jeeklite | 78 wt. parts |
| (2) White Carbon | 15 wt. parts |
| (3) Lavelin S (trade name for a sodium napthalene sulfonate-formaldehyde condensate produced by Daiichi Kogyo Seiyaku Co., Ltd.) | 2 wt. parts |
| (4) Sorpol 5039 (trade name for a sulfate of polyoxyethylene alkylaryl ether produced by Toho Chemical Co., Ltd.) | 5 wt. parts |

Components (1) to (4) were mixed and the mixture obtained was then mixed with γ-[4-(3,5-dichloropyridyl-2-oxy)phenoxy]valeric acid in a ratio of 4:1 by weight to form a wettable powder.

FORMULATION EXAMPLE 3

| | |
|---|---|
| (1) Bentonite | 58 wt. parts |
| (2) Jeeklite | 30 wt. parts |
| (3) Sodium Ligninsulfonate | 5 wt. parts |

Components (1) to (3) were mixed and granulated. A solution prepared by diluting 7 wt. parts of methyl-γ-[4-(3,5-dichloropyridyl-2-oxy)phenoxy]valerate with acetone was sprayed on the granulated components to form granules.

FORMULATION EXAMPLE 4

| | |
|---|---|
| (1) γ-[4-(3,5-Dichloropyridyl-2-oxy)-phenoxy]valeramide | 3 wt. parts |
| (2) Kaolin | 50 wt. parts |
| (3) Talc | 46 wt. parts |
| (4) Lavelin S | 1 wt. parts |

Components (1) to (4) were mixed and pulverized to form a dust.

FORMULATION EXAMPLE 5

| | |
|---|---|
| (1) Sodium-γ-[4-(3,5-dichloropyridyl-2-oxy)-phenoxy]valerate | 20 wt. parts |
| (2) N-Methyl-2-pyrrolidone | 15 wt. parts |
| (3) Polyoxyethylene Alkylaryl Ether | 5 wt. parts |
| (4) Ethyl Alcohol | 60 wt. parts |

Components (1) to (4) were uniformly mixed to form a water-miscible solution.

The herbicidal activity of the compound of this invention was tested as shown below and the results obtained are also shown below.

TEST EXAMPLE 1

Each 1/3,000 are (1/30 $m^2$) flat was charged with soil to provide upland farm conditions. Predetermined amounts of seeds of edible barnyard grass, radish and soybeans were sown and covered with soil containing seeds of large crabgrass (*Digitaria adscendens* HENR.), green foxtail (*Setaria viridis* BEAUV.) and barnyard grass (*Echinochloa crus-galli* BEAUV.) as gramineous weeds to a thickness of about 1 cm. Three days after sowing, an aqueous dispersion of each of the compounds shown in Table 1 was sprayed thereon, and the growth of the weeds and crops was visually evaluated twenty days after the spraying. The results obtained are shown in Table 1. The degree of growth inhibition shown in Table 1 was evaluated on a scale of 10 grades in which 10 indicates that growth was completely inhibited and 1 indicates no inhibition.

Table 1

| Compound No. | Amount of Active Ingredient | Degree of Growth inhibition | | | |
|---|---|---|---|---|---|
| | | Edible Barnyard Grass | Radish | Soybeans | Gramineous Weeds |
| | (g/are) | | | | |
| 1 | 100 | 10 | 1 | 1 | 10 |
| | 50 | 10 | 1 | 1 | 10 |
| 2 | 100 | 10 | 1 | 1 | 10 |
| | 50 | 10 | 1 | 1 | 10 |
| 3 | 100 | 10 | 1 | 1 | 10 |
| | 50 | 10 | 1 | 1 | 10 |
| 5 | 100 | 10 | 1 | 1 | 10 |
| | 50 | 10 | 1 | 1 | 10 |
| 6 | 100 | 10 | 1 | 1 | 10 |
| | 50 | 10 | 1 | 1 | 10 |
| 7 | 100 | 10 | 1 | 1 | 10 |
| | 50 | 10 | 1 | 1 | 10 |
| 8 | 100 | 10 | 1 | 1 | 10 |
| | 50 | 7 | 1 | 1 | 8 |
| 9 | 100 | 10 | 1 | 1 | 10 |
| | 50 | 10 | 1 | 1 | 10 |
| 10 | 100 | 9 | 1 | 1 | 10 |
| | 50 | 7 | 1 | 1 | 7 |
| 12 | 100 | 9 | 1 | 1 | 10 |
| | 50 | 7 | 1 | 1 | 8 |

TEST EXAMPLE 2

Each 1/10,000 are (1/100 m²) pot was charged with soil to provide upland farm conditions. Predetermined amounts of seeds of edible barnyard grass, radish and soybeans were sown and covered with soil to a thickness of about 1 cm. When the edible barnyard grass reached a two-leaf stage, an aqueous dispersion of each of the compounds shown in Table 2 was applied to foliage in a predetermined amount. Twenty days after treatment with the dispersion, the growth of weeds and crops was visually evaluated, and the degree of growth inhibition was evaluated on the same scale as in Test Example 1. The results obtained are shown in Table 2.

TABLE 2

| Compound No. | Concentration of Active Ingredient | Degree of Growth Inhibition | | |
|---|---|---|---|---|
| | | Edible Barnyard Grass | Radish | Soybeans |
| | (ppm) | | | |
| 1 | 2,000 | 10 | 1 | 1 |
| | 1,000 | 10 | 1 | 1 |
| 2 | 2,000 | 10 | 1 | 1 |
| | 1,000 | 10 | 1 | 1 |
| 3 | 2,000 | 10 | 1 | 1 |
| | 1,000 | 10 | 1 | 1 |
| 5 | 2,000 | 10 | 1 | 1 |
| | 1,000 | 10 | 1 | 1 |
| 6 | 2,000 | 10 | 1 | 1 |
| | 1,000 | 10 | 1 | 1 |
| 7 | 2,000 | 10 | 2 | 3 |
| | 1,000 | 10 | 1 | 1 |
| 8 | 2,000 | 10 | 1 | 2 |
| | 1,000 | 10 | 1 | 1 |
| 9 | 2,000 | 10 | 1 | 1 |
| | 1,000 | 10 | 1 | 1 |
| 10 | 2,000 | 10 | 1 | 1 |
| | 1,000 | 10 | 1 | 1 |
| 12 | 2,000 | 10 | 1 | 1 |
| | 1,000 | 10 | 1 | 1 |

TEST EXAMPLE 3

Each 1/10,000 are (1/100 m²) pot was charged with soil and completely saturated with water. A predetermined amount of air-dried seeds of barnyard grass was sown and lightly covered with soil. When the barnyard grass germinated above the ground, water was put into the pot to a depth of 3 cm to provide flooded conditions, and an aqueous dispersion of each of the compounds shown in Table 3 was poured into the pot. Fourteen days after treatment with the dispersion, the surviving barnyard grass in the pot was pulled out, dried in air, and weighed. The percentage of the amount of surviving weeds based on the untreated pot was calculated, and the degree of growth determined (with 0% meaning no growth and 100% no inhibition). The results obtained are shown in Table 3.

TABLE 3

| Compound No. | Degree of Growth (%) | |
|---|---|---|
| | Amount of Active Ingredient (g/are) | |
| | 2.5 | 1.25 |
| 3 | 0 | 0 |
| 5 | 0 | 0 |
| 6 | 0 | 0 |

While the invention has been described in detail and with reference to specific embodiments thereof, it will be apparent to one skilled in the art that various changes and modifications can be made therein without departing from the spirit and scope thereof.

What is claimed is:

1. A compound having the formula (I):

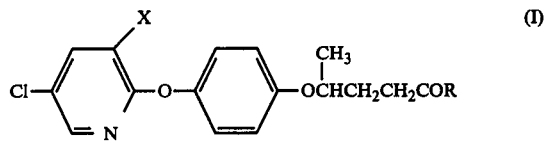

wherein X is a hydrogen atom or a chlorine atom; and R is a hydroxy group, an —O-cation group, a ($C_1$–$C_4$)alkoxy group, a ($C_1$–$C_4$)alkylthio group, a benzyloxy group, or an amino group which may be substituted with a ($C_1$–$C_4$)alkyl group(s), a phenyl group or a pyridine-2-yl group.

2. The compound of claim 1, wherein R is a hydroxy group, an —O-cation group, a ($C_1$–$C_4$)alkoxy group or a benzyloxy group.

3. The compound of claim 1, wherein R is a hydroxy group, an —O-cation group or a ($C_1$–$C_4$)alkoxy group.

4. The compound of claim 2, wherein X is a chlorine atom.

5. The compound of claim 4, wherein said compound is γ-[4-(3,5-dichloropyridyl-2-oxy)phenoxy]valeric acid.

6. The compound of claim 4, wherein said compound is sodium-γ-[4-(3,5-dichloropyridyl-2-oxy)-phenoxy]-valerate.

7. The compound of claim 4, wherein said compound is methyl-γ-[4-(3,5-dichloropyridyl-2-oxy)-phenoxy]-valerate.

8. A herbicidal composition comprising a herbicidally effective amount of at least one compound having the formula (I):

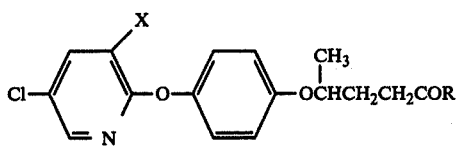

wherein X is a hydrogen atom or a chlorine atom; and R is a hydroxy group, an —O-cation group, a (C$_1$–C$_4$)alkoxy group, a (C$_1$–C$_4$)alkylthio group, a benzyloxy group, or an amino group which may be substituted with a (C$_1$–C$_4$)alkyl group(s), a phenyl group or a pyridine-2-yl group, as an active ingredient and an agriculturally acceptable adjuvant.

9. The herbicidal composition of claim 8, wherein R is a hydroxy group, an —O-cation group, a (C$_1$–C$_4$)alkoxy group or a benzyloxy group.

10. The herbicidal composition of claim 8, wherein R is a hydroxy group, an —O-cation group or a (C$_1$–C$_4$)alkoxy group.

11. The herbicidal composition of claim 9, wherein X is a chlorine atom.

12. The herbicidal composition of claim 11, wherein said compound is γ-[4-(3,5-dichloropyridyl-2-oxy)phenoxy]valeric acid.

13. The herbicidal composition of claim 11, wherein said compound is sodium-γ-[4-(3,5-dichloropyridyl-2-oxy)phenoxy]valerate.

14. The herbicidal composition of claim 11, wherein said compound is methyl-γ-[4-(3,5-dichloropyridyl-2-oxy)phenoxy]valerate.

15. A method for controlling noxious weeds in the presence of cultivated crops which comprises applying a herbicidally effective amount of a herbicidal composition of claim 8.

* * * * *